Figure 1:
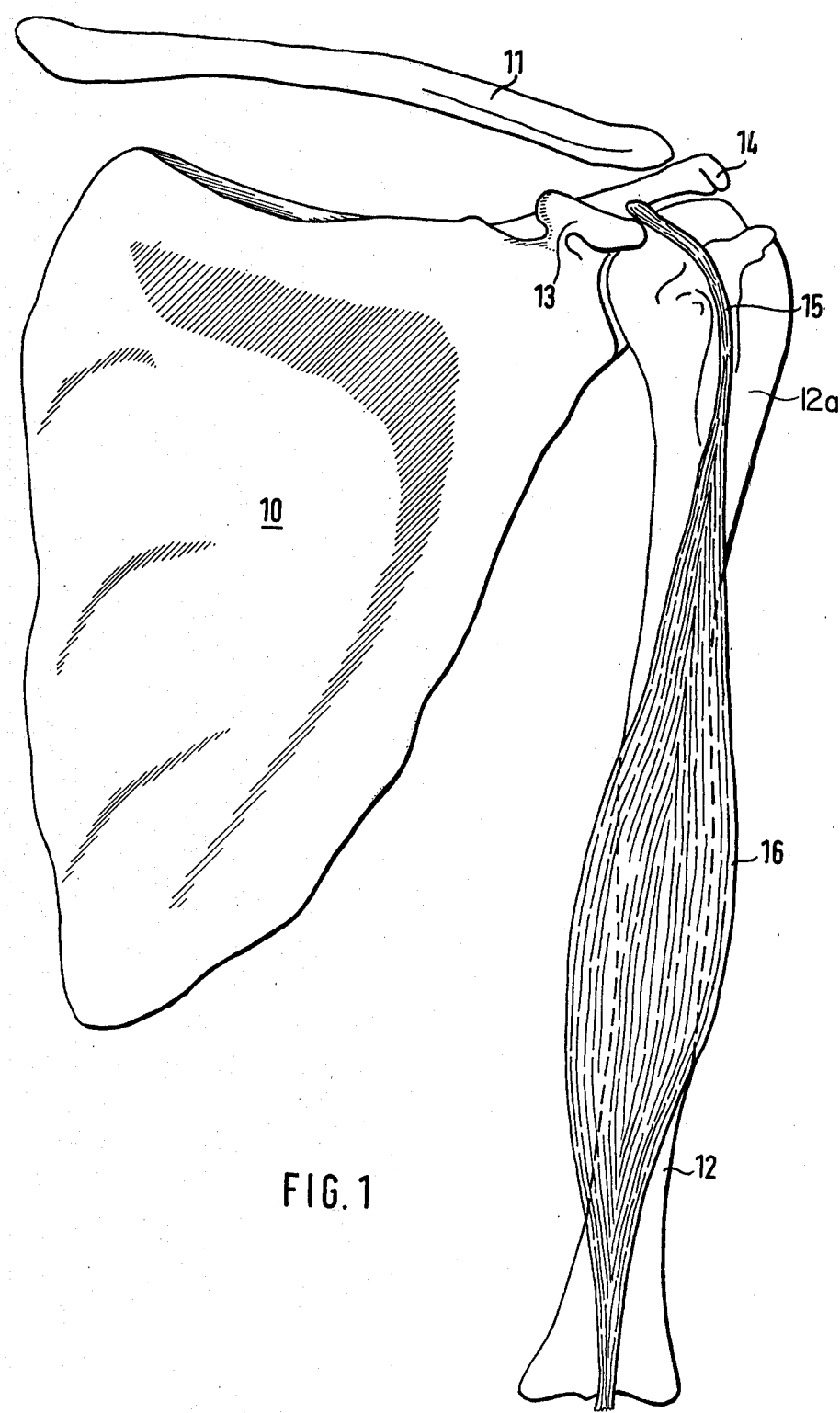

United States Patent [19]

Schneider

[11] 4,355,427
[45] Oct. 26, 1982

[54] ARTIFICIAL HUMERUS HEAD

[76] Inventor: Wolfgang Schneider, Weddigenufer 12, D-4900 Herford, Fed. Rep. of Germany

[21] Appl. No.: 215,979

[22] Filed: Dec. 12, 1980

[51] Int. Cl.³ .............................................. A61F 1/03
[52] U.S. Cl. ..................................... 3/1.91; 128/92 C
[58] Field of Search .................... 3/1.91, 1.911, 1.912, 3/1.913; 128/92 C, 92 CA

[56] References Cited

U.S. PATENT DOCUMENTS 2,765,787 10/1956 Pellet ............................... 3/1.913 X
3,909,854 10/1975 Martinez ...................... 128/92 C X
3,924,276 12/1975 Eaton ............................ 128/92 C X
3,991,425 11/1976 Martin et al. ................. 128/92 C X Primary Examiner—Clifford D. Crowder
Attorney, Agent, or Firm—Pollock, Vande Sande & Priddy

[57] ABSTRACT

An artificial humerus head has a groove in its exterior surface for receiving the long biceps tendon. A cover bridges the groove to form an elongated open-end channel for the tendon and makes it possible to arrange the long biceps tendon in the channel without separation thereof from the head.

7 Claims, 6 Drawing Figures

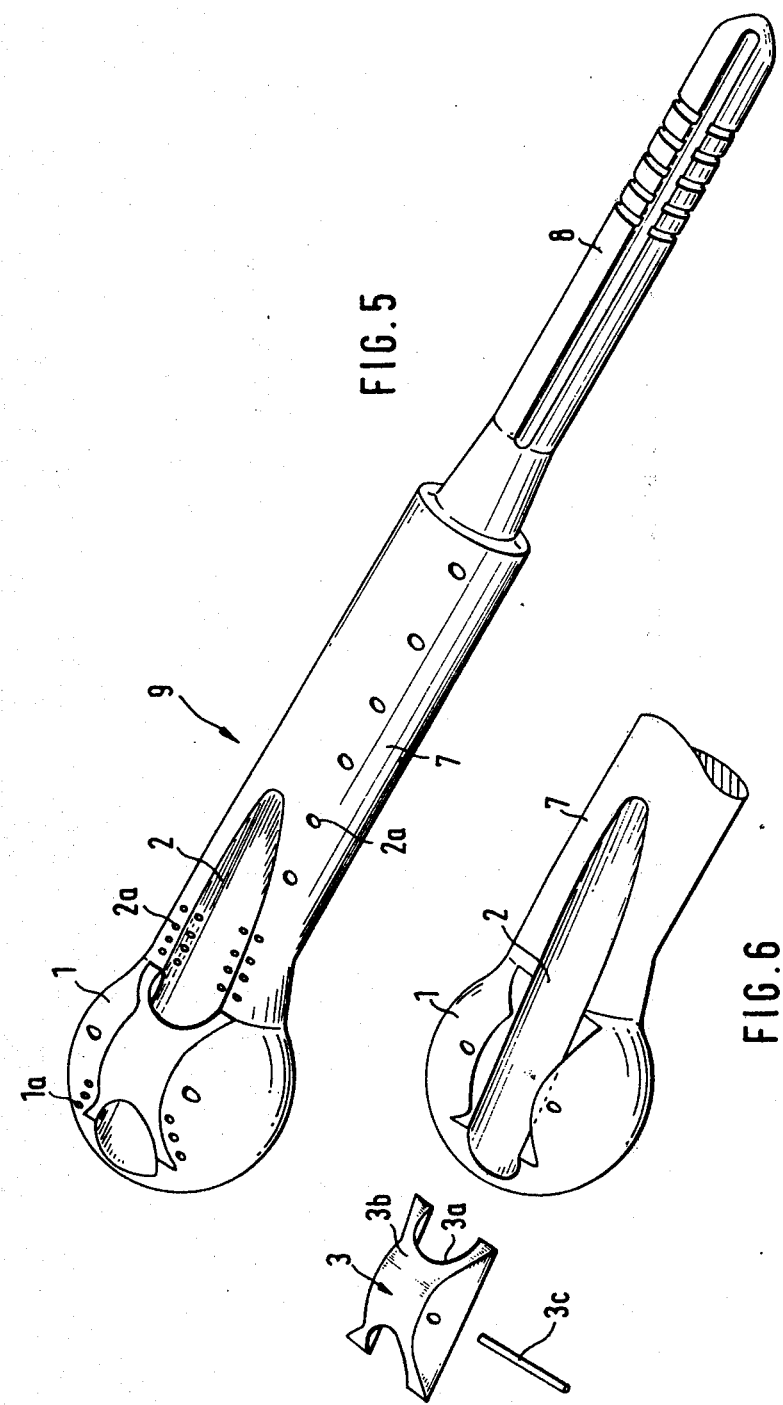

ARTIFICIAL HUMERUS HEAD

The invention concerns an artificial humerus head having a pin for insertion into the shaft of the humerus, and an artificial shaft in continuation of the humerus shaft, and a substantially spherical artificial head which has a channel arranged at a slight angle to the longitudinal axis of the artificial member.

Known artificial humerus heads of this type (e.g. DE-GM 71 46 082) after resection of the natural humerus head, are fitted with the pin in the remaining shaft of the humerus and secured thereto. Before resection of the natural humerus head and before the pin is inserted, it has previously been necessary and usual to separate the long biceps tendon from the projection to which it is secured. After insertion of the artificial member, the long biceps tendon is then connected to the head thereof. The result of this is that the arm can only be slightly stressed, and, furthermore, that the head of the artificial member is easily dislodged from the intended normal position because it is no longer held in its natural, intended position by the biceps tendon.

The purpose of the invention is to provide an artificial humerus head which does not exhibit the disadvantages of the known artificial members described, and which is suitable for the construction of a practically fully operable shoulder joint.

To achieve this purpose it is suggested, according to the invention, that a channel extends throughout the artificial humerus head and is formed to receive the biceps tendon, and is provided with an external cover means.

The provision of a channel in the head of the artificial member permits the insertion of the member without the previously necessary prior separation of the long biceps tendon. With the new artificial member it is possible to leave the biceps tendon unaltered, and to lead it through the said channel in the artificial member. The external cover means for the channel forms a reliable retaining means for the biceps tendon, so that it can not spring out of the channel.

In a preferred embodiment the cover means consists of an element which completely bridges the channel cross-section, can be secured to the head of the artificial member, and takes the form of a separate part. Such a construction permits an especially simple insertion of the artificial member and closure of the channel after lodging the biceps tendon in the channel provided.

In a preferred improvement of the invention, the cover means is a slide which can be inserted into a guide running at least substantially parallel to the channel, and which is immovably secured to the head of the artificial member in radial direction by means of form locking.

Preferably the slide is provided with a locking pin for securing the slide in its final position.

An embodiment in which the head of the artificial member and the slide are formed with dovetail guide means has proved particularly advantageous.

Finally it is suggested according to the invention that the inner surface of the slide forms the wall of the channel, and the outer surface thereof is a continuation of the outer contour of the head on the artificial member.

Figure 2:
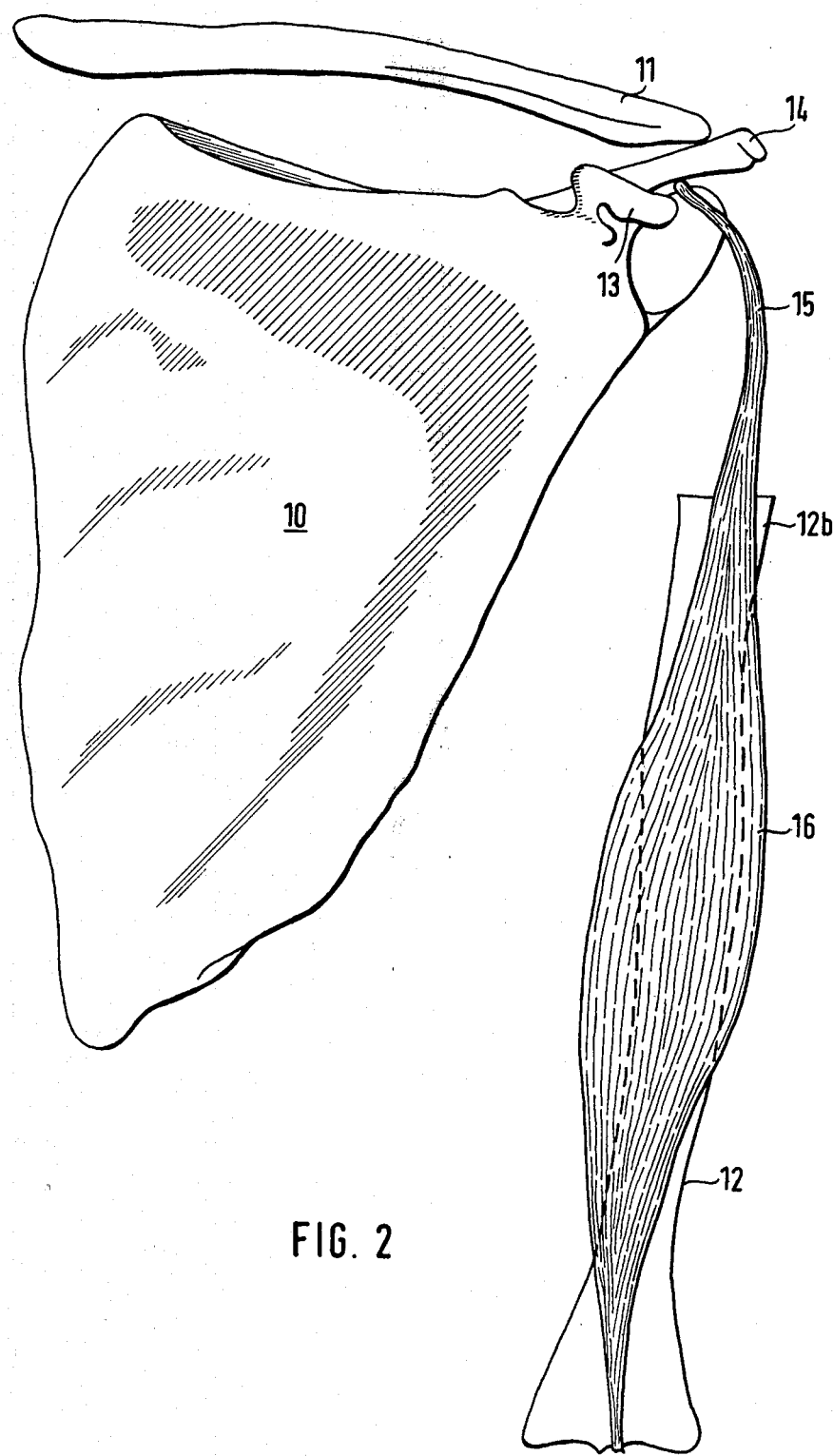
Figure 3:
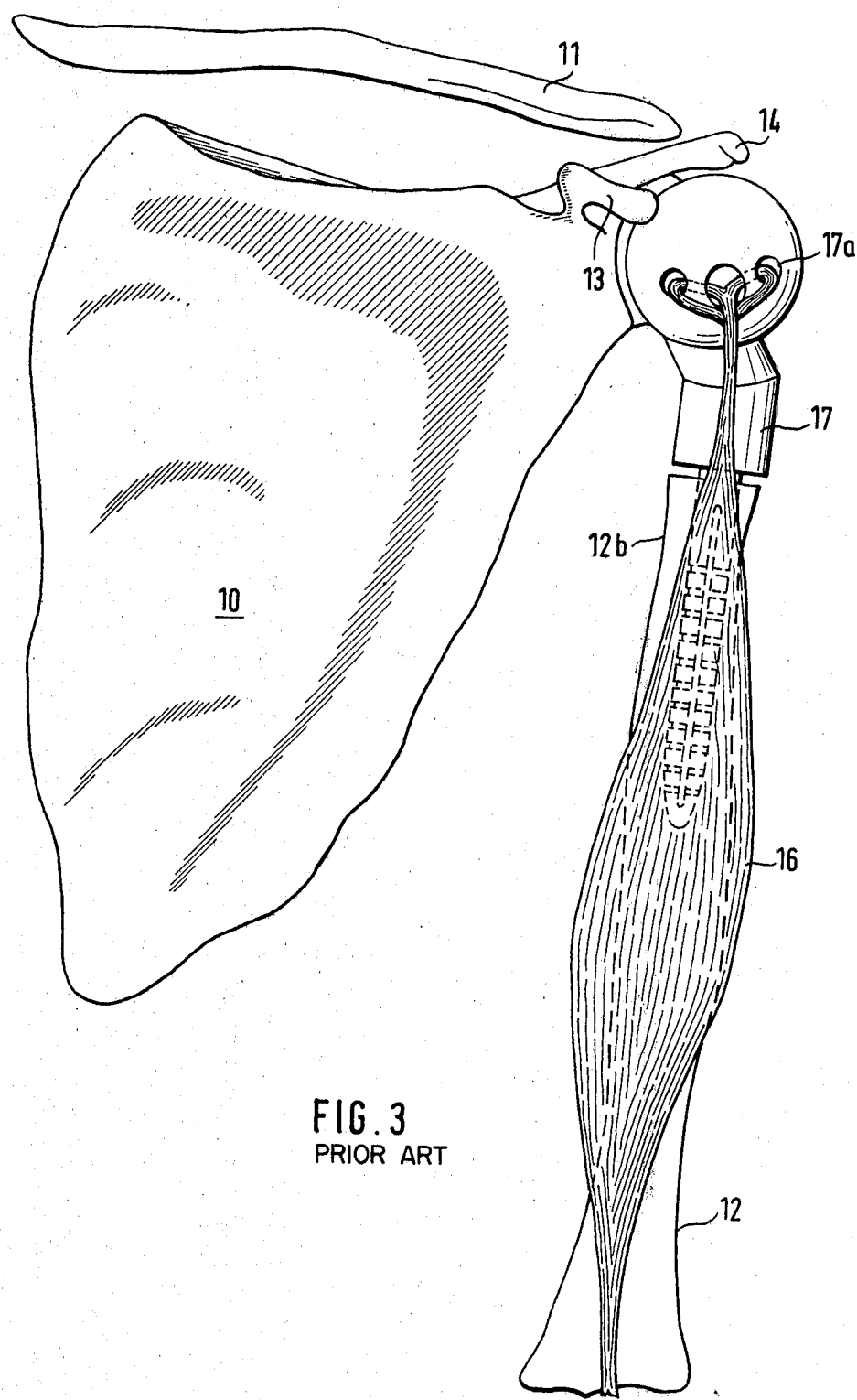
Figure 4:
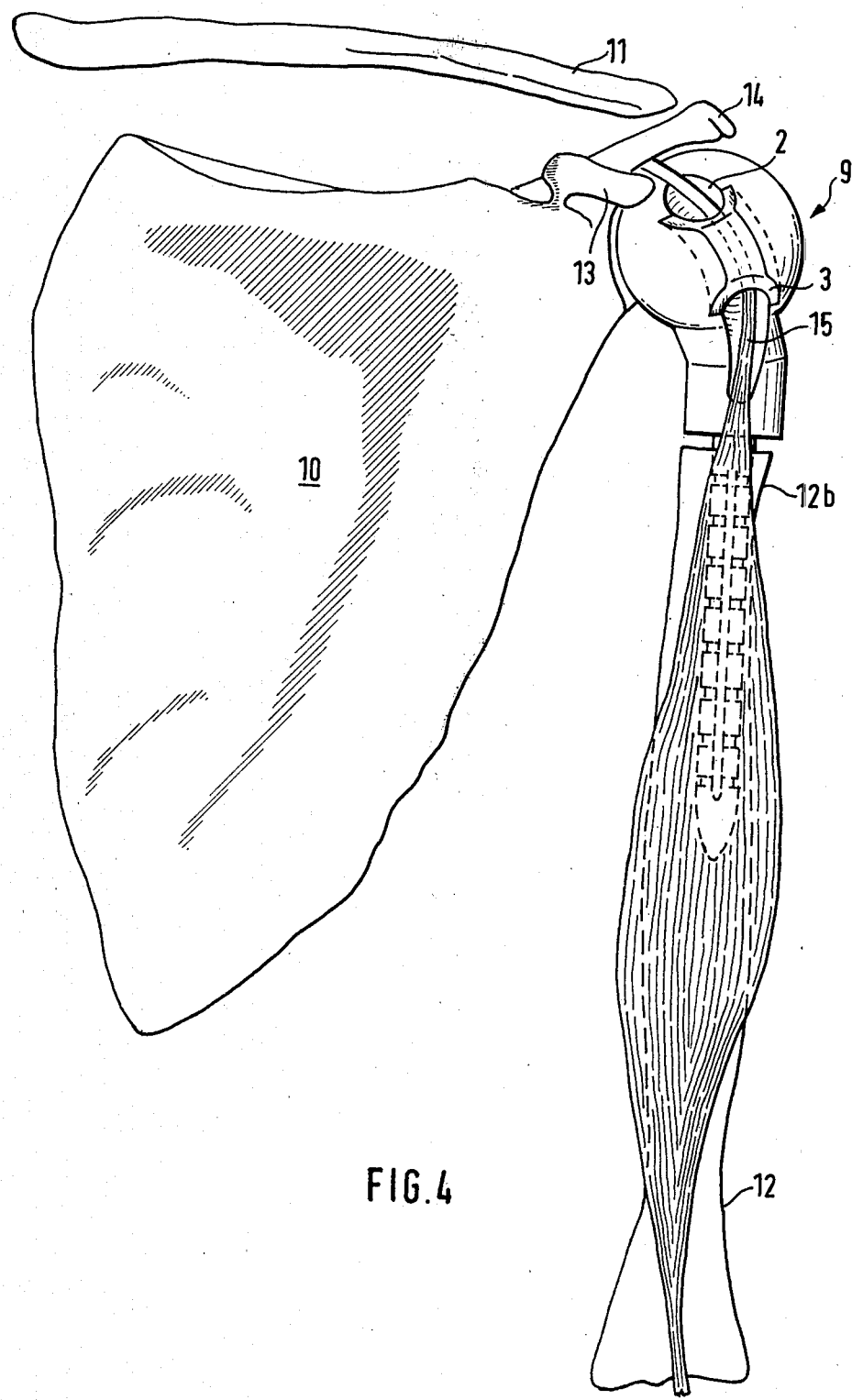

A preferred embodiment of the invention will now be described in detail with the aid of the drawings, wherein:

FIG. 1 is an illustration of the natural anatomy in the region of the shoulder joint, FIG. 2 is an illustration according to FIG. 1 after resection of the natural humerus head, FIG. 3 is an illustration similar to FIG. 2 showing use of a prior art artificial member, FIG. 4 illustrates the anatomy according to FIGS. 1 to 3, but using the artificial member of the present invention, FIG. 5 is a perspective illustration of the new artificial member with the slide inserted, and FIG. 6 is a perspective illustration of the new artificial member with the slide and securing pin in exploded view.

In FIG. 1 the shoulder blade 10, the collar bone 11, the humerus 12, the projection 13 and the acromion 14 are visible. The tendon 15 of the long biceps 16 is connected to the acromion 14.

FIG. 2 is an illustration according to FIG. 1 wherein the humerus head 12a has been sawn off at the humerus shaft 12b.

In FIG. 3 the installed condition of a prior art artificial humerus head 17 can be seen. The known artificial humerus head 17 has a through hole 17a in which the end of the long biceps tendon, separated from the acromion 14, is secured.

FIG. 4 shows an illustration analagous to FIG. 3, wherein the artificial member according to the invention, indicated generally by the numeral 9, has been installed. It can be seen in FIG. 4 that the long biceps tendon 15 runs through a channel 2, and that the exterior of the channel 2 is covered by means of a slide 3. The long biceps tendon 15 is freely moveable within the covered channel 2.

The artificial humerus head, generally indicated at 9, has the head 1, a downwardly extending shaft 7 and a pin 8 for insertion into the humerus shaft. The channel 2 passes through the artificial head 1 and part of the adjacent shaft 7 and can be covered in the region of the artificial head by means of the slide 3. In the head 1 dovetail guide grooves are provided, about parallel to the longitudinal axis of the channel 2, in which the correspondingly formed slide 3 can be inserted in the direction of the channel axis. When installed, the slide is secured in position by means of a locking pin 3c. The inner surface 3a of the slide 3 forms the wall of the channel 2. The outer surface 3b of the slide 3 is a continuation of the outer contour of the artificial head 1.

Various recesses 1a and 2a are provided in the head 1 and the shaft 2, which serve to secure the shoulder covering.

I claim:

1. An artificial humerus head comprising an elongated unitary member having a pin at one end thereof for insertion into the shaft of a humerus, a substantially spherical head at the other end thereof, and a shaft between said pin and head adapted to act as a continuation of the humerus when said pin is inserted into the shaft of the humerus, said spherical head having an elongated groove formed in its exterior surface for longitudinally receiving the long biceps tendon, said groove extending generally in the direction of elongation of said member between spaced points on the outer periphery of said head and being oriented at a slight angle to the longitudinal axis of said elongated member, and a cover member covering said groove and cooperating with said groove to form an open-ended, enclosed channel for the long biceps tendon extending through said head generally in the direction of elongation of said member.

2. The artificial humerus head of claim 1 wherein a portion of said groove extends into the exterior surface of the shaft of said elongated member.

3. The artificial humerus head of claim 1 or 2 wherein said cover member is an element separate from said head, and means for securing said cover member to said head in overlying relation to said groove.

4. The artificial humerus head of claim 1 or 2 wherein said cover member is an elongated element separate from said head, said cover member being slidably insertible into said groove with the opposing exterior sides of said elongated cover member engaging the interior opposing sides of said elongated groove.

5. The artificial humerus head of claim 4 including a locking pin for securing said slidable cover member in fixed position relative to said groove.

6. The artificial humerus head of claim 4 wherein said exterior sides of said cover member and said interior sides of said groove exhibit complementary dovetail configurations.

7. The artificial humerus head of claim 1 or 2 wherein the outer surface of said cover means is contoured as a smooth continuation of the outer contour of said head.

* * * * *